US006316594B1

US006316594B1

(12) United States Patent
Kim et al.

(10) Patent No.: US 6,316,594 B1
(45) Date of Patent: Nov. 13, 2001

(54) ANTIMICROBIAL PEPTIDE ISOLATED FROM PARASILURUS ASOTUS AND ITS USES

(75) Inventors: Sun Chang Kim; In Yup Park; Chan Bae Park, all of Taejon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/381,601

(22) PCT Filed: Mar. 22, 1999

(86) PCT No.: PCT/KR99/00126

§ 371 Date: Jan. 4, 2000

§ 102(e) Date: Jan. 4, 2000

(87) PCT Pub. No.: WO99/48912

PCT Pub. Date: Sep. 30, 1999

(30) Foreign Application Priority Data

Mar. 25, 1998 (KR) ................................. 98-10270
Feb. 12, 1999 (KR) .................................. 99-5078

(51) Int. Cl.[7] ........................................ C07K 7/00
(52) U.S. Cl. ................... 530/326; 514/13; 514/14; 514/2; 530/324
(58) Field of Search ................... 530/326, 324; 514/13, 14, 2

(56) References Cited

FOREIGN PATENT DOCUMENTS

99/48912 * 9/1999 (WO) .

OTHER PUBLICATIONS

D. Robinette et al., Antimicrobial Activity in the Skin of the Channel Catfish Ictabaus Punctatus: Characterization of Broad–Spectrum Histone–like Antimicrobial Proteins. Cellular and Molecular Life Sciences, 1998, vol. 54, pp. 467–475.

Wouters–Tyron, D. et al., The Amino Acid Sequence of Histone H2A from Cuttlefish Sepia Officiralis. European Journal of Biochemistry, May (1) 1982, vol. 124, No. 1 pp. 489–498; ISSN0014–2956.

Cole, A.M., Isolation and Characterization of Pleurocidin, an Antimicrobial Peptide in the Skin Secretions of Winter Flounder. The Journal of Biological Chemistry, Apr. 25, 1997, vol. 272, No. 18, pp. 12008–12013, ISSN0021–9358.

* cited by examiner

Primary Examiner—Christopher S. F. Low
Assistant Examiner—David Lukton
(74) Attorney, Agent, or Firm—Morrison & Foerster LLP

(57) ABSTRACT

Disclosed is a novel antimicrobial peptide, named parasin I, which is isolated from catfish. Catfish produce a strong antimicrobial peptide in the epithelial mucosal layer upon epidermal injury to protect against the invasion of microorganisms. It is 2000.4 Da in molecular mass and consist of 19 amino acid residues, represented by Lys-Gly-Arg-Gly-Lys-Gln-Gly-Gly-Lys-Val-Arg-Ala-Lys-Ala-Lys-Thr-Arg-Ser-Ser (SEQ ID NO: 1) Parasin I shows exceptionally potent antimicrobial activity against a broad spectrum of micrroorganisms, including Gram-positive and Gram-negative bacteria and fungui, without any hemolytic activity. Its synthetic derivatives also have potent activity. Therefore, parasin I and its derivatives can be used as wound healing agent, trauma curing agent, mouthwash, eyewash, etc.

8 Claims, 6 Drawing Sheets

FIG. 3

| Peptide | Amino acid sequence |
|---|---|
| Parasin I | K G R G K Q G G K V R A K A K T R S S |
| Buforin I | A G R G K Q G G K V R A K A K T R S S R A G L Q F ... |
| Human histone H2A.5 | S G R G K Q G G K A R A K A K T R S S R A G L Q F ... |

SEQUENCE LISTING

<160> NUMBER OF SEQ ID NOS: 6

<210> SEQ ID NO 1
<211> LENGTH: 19
<212> TYPE: PRT
<213> ORGANISM: Parasilurus asotus

<400> SEQUENCE: 1

Lys Gly Arg Gly Lys Gln Gly Gly Lys Val Arg Ala Lys Ala Lys Thr
 1               5                  10                  15

Arg Ser Ser

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:
      recombination of the amino acid sequence isolated from
      parasilurus asotus

<400> SEQUENCE: 2

Lys Gly Arg Gly Lys Gln Gly Gly Lys Val Arg Ala Lys Ala Lys Thr
 1               5                  10                  15

Arg

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence:
      recombination of the amino acid sequence isolated from
      parasilurus asotus

<400> SEQUENCE: 3

Lys Gly Arg Gly Lys Gln Gly Gly Lys Val Arg Ala Lys Ala Lys
 1               5                  10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:
      recombination of the amino acid sequence isolated from
      parasilurus asotus

<400> SEQUENCE: 4

Ser Ser Arg Thr Lys Ala Lys Ala Arg Val Lys Gly Gly Gln Lys Gly
 1               5                  10                  15

Arg Gly Lys

<210> SEQ ID NO 5
<211> LENGTH: 25
<212> TYPE: PRT

-continued

```
<213> ORGANISM: Unknown Organism
<220> FEATURE:
<223> OTHER INFORMATION: Description of Unknown Organism: Buforin I

<400> SEQUENCE: 5

Ala Gly Arg Gly Lys Gln Gly Gly Lys Val Arg Ala Lys Ala Lys Thr
 1               5                  10                  15

Arg Ser Ser Arg Ala Gly Leu Gln Phe
                20                  25

<210> SEQ ID NO 6
<211> LENGTH: 25
<212> TYPE: PRT
<213> ORGANISM: Homo sapiens

<400> SEQUENCE: 6

Ser Gly Arg Gly Lys Gln Gly Gly Lys Ala Arg Ala Lys Ala Lys Thr
 1               5                  10                  15

Arg Ser Ser Arg Ala Gly Leu Gln Phe
                20                  25
```

ANTIMICROBIAL PEPTIDE ISOLATED FROM *PARASILURUS ASOTUS* AND ITS USES

TECHNICAL FIELD

The present invention relates to a novel peptide which has a potent antimicrobial activity against a broad spectrum of microorganisms. More particularly, the present invention relates to an antimicrobial peptide, named parasin I, isolated from catfish with the scientific name of *Parasilurus asotus* and its uses.

BACKGROUND ART

The research data for the last decade have revealed that, besides their immune systems, almost all living organisms have an additional defense system against invading pathogenic microorganisms. They produce antimicrobial peptides in their bodies and use them as a defense means against pathogenic microorganisms.

Since the discovery of cecropin, a novel antimicrobial peptide, in silkworm larvae as a result of a study on the defense mechanism of insects against the invasion of microorganisms, the importance of peptides as physiologically active materials has been greatly recognized.

Thus far, as many as about 450 antimicrobial peptides have been found from amphibians, insects, mammals, plants, microorganisms and fishes. These antimicrobial peptides are known to be different in their sizes and amino acid sequences, but similar in their antimicrobial mechanism. Representative antimicrobial peptides can be exemplified by cecropin, magainin, bombinin, defensin, tachyplesin, and buforin. They are composed of 17–24 amino acids, showing antimicrobial activity against a broad spectrum of microorganisms, including Gram-negative bacteria, Gram-positive bacteria, protozoa and fungi. Some of them are effective against both cancer cells and viruses. For instance, magainin, consisting of 23 amino acids, was isolated from the skin of an amphibian and is reported not only to defend against pathogenic bacteria, but to kill human lung cancer cells (Zasloff, M. (1987) Proc. Natl. Acad. Sci., U.S.A. 84, 5449–5453).

Most of the antimicrobial peptides kill target cells rapidly and specifically, and have unusually broad activity spectra (Park, C. B., et al., (1997) FEBS Lett. 411, 173–178; Park, C. B., et al., (1996) Biochem. Biophys. Res. Comm. 218, 408–413). In addition to the microbicidal activity, antimicrobial peptides are reported to have other functions such as promotion of wound healing, stimulation of monocyte chemotaxis and inhibition of cytokine response.

Mucosal surfaces of living organisms are under constant attack from microorganisms. However, invasive infections are rare, remain localized and heal rapidly. Recent reports have established antimicrobial peptides as host-defense effector molecules which protect the mucosal epithelia from the invading microbes (Bevins, C. L. (1994) Ciba Found. Symp., 186, 250–260). Examples of these agents of mucosal immunity include andropin from the ductal epithelial cells of the reproductive tract of Drosophila, magainins from the mucosal skin surface and the gastrointestinal tract of *Xenopus laevis*, buforin I from the Bufo bufo gargarizans, tracheal antimicrobial peptide from bovine tracheal mucosa, and pleurocidin from *Pleuronectes americanus* (Cole, A. M., et al., (1997) J. Biol. Chem., 272, 12008–12013). While many antimicrobial peptides have been reported to be in the mucosal layer of amphibians, insects and mammals (Park, C. B. et al., (1996) supra; Samakovlis, C., et al., (1991) EMBO J. 10, 163–169; Diamond, G., et al., (1991) Proc. Natl. Acad. Sci., U.S.A., 88, 3952–3956), only a few have been found in the mucosal layer of aquatic organisms (Park, C. B., et al., (1997) supra; Cole, A. M., et al., (1997) supra; Chen, H., et al., (1998) FEBS Lett., 236, 462–466).

DISCLOSURE OF THE INVENTION

With the background in mind, the present inventors paid attention to the catfish skin which is not easily infected with pathogenic microorganisms. The intensive and thorough research on antimicrobial peptides, performed by the present inventors, resulted in the finding that a peptide isolated from the injured epithelial mucosal layer of catfish has a potent antimicrobial activity against various microbes.

It is an object of the present invention to provide a novel antimicrobial peptide which shows potent antimicrobial activity against a broad spectrum of microorganisms.

It is another object of the present invention to provide uses of the peptide as pharmaceutically available antimicrobial agents.

The above and other objects are attained in the novel antimicrobial peptide, parasin I, isolated from catfish, which comprises the whole amino acid sequence represented by the following formula I:

K G R G K Q G G K V R A K A K T R S S (SEQ ID NO: 1)[I]

or a derivative form thereof.

BRIEF DESCRIPTION OF THE DRAWINGS

FIG. 3 shows the homology between the amino acid sequences of parasin I, buforin I and human histone H2A.5.

BEST MODE FOR CARRYING OUT THE INVENTION

Figure 1A:
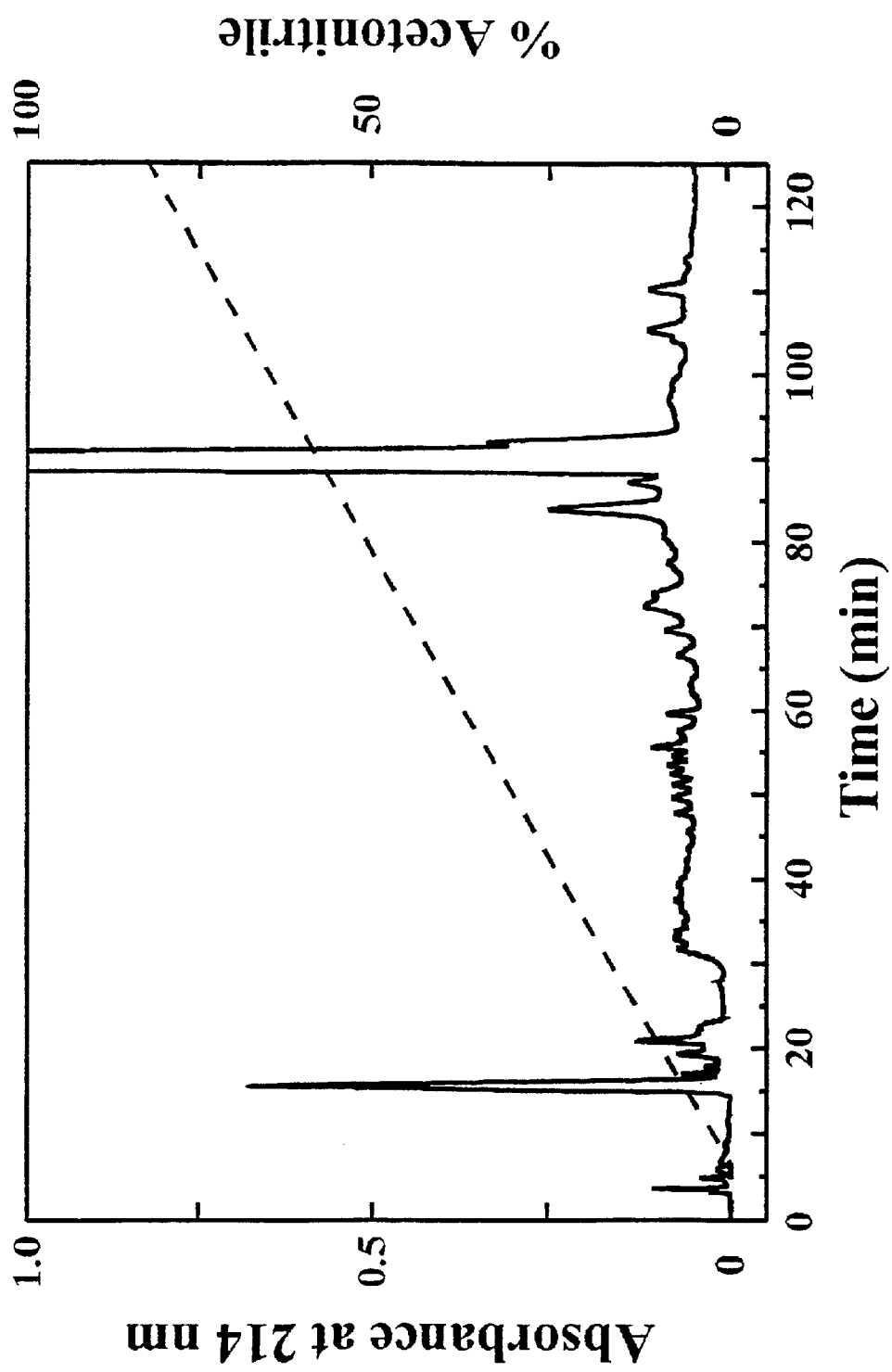
FIGS. 1*a* and 1*b* are reverse-phase HPLC spectra for the peptides isolated from the wounded skin and unwounded skin of catfish, respectively.

Generally, antimicrobial peptides have potent inhibitory activity against a wide spectrum of microorganisms. Also, antimicrobial peptides exert their killing effects on invading pathogenic microbes, but not on the host cells. Therefore, when applied to men, they are harmless to the human body.

Antibiotics show potent killing activity, but microbes are becoming resistant against antibiotics. In contrast, antimicrobial peptides are thought not to cause such a problem by virtue of different mechanisms in antimicrobial activity from those of antibiotics.

Because antimicrobial peptides do not undergo secondary modification, such as glycosylation, they can be mass-produced through genetic engineering techniques. Another advantage of antimicrobial peptides is that they are physicochemically stable to heat, acid, alkali, etc. Therefore, they are of great industrial applicability in the pharmacological and food industries.

The present invention pertains to the isolation and characterization of a potent antimicrobial peptide from catfish.

For this, first, catfish was injured by scratching the skin with a sandpaper, followed by collecting the mucus of the proteinaceous epithelial mucosal layer.

Subsequently, the peptides in the mucus are concentrated using, for example, Sep-Pak C18 cartridge and purified using, for example, C18 reverse-phase high-performance liquid chromatography (HPLC). The purified peptide can be measured for its molecular weight with the aid of, for example, matrix associated laser desorption ionization mass spectroscopy (MALDI-MS) and determined for its amino acid sequence by Edman degradation.

In order to determine the effective length of parasin I in microbial activity, peptides with various lengths are synthesized on the basis of the analyzed amino acid sequence. It was found that the synthetic derivatives which are deficient of 2 and 4 carboxyl terminal residues of the natural parasin I, are of potent antimicrobial activity. In addition, the peptide having the amino acid sequence in the reverse order to the amino acid sequence of the natural parasin I, also has a potent antimicrobial activity. In fact, minimal inhibitory concentration data demonstrate that they are almost the same in antimicrobial activity.

For microbial activity assay, a radial diffusion method was taken using *Bacillus subtilis* ATCC 62037. To determine whether parasin I can be applied to the human body, the hemolytic activity of parasin I was assayed. From this assay, parasin I was found to be applied as antimicrobial agents for the human body, safely.

More scientific results are obtained by use of a spectropolarimeter which is useful to determine the secondary structure of parasin.

All of the microorganisms used in the invention were obtained from the American Type Culture Collection (ATCC) Used were *Bacillus subtilis* ATCC 62037, *Staphylococcus aureus* ATCC 15752, *Streptococcus mutans* ATCC 25175, *Pseudomonas putida* ATCC 17426, *Escherichia coli* ATCC 27325, *Salmonella typhimurium* ATCC 15277, Seratia sp. ATCC 21074, *Cryptococcus neoformans* ATCC 34881, *Saccharomyces cerevisiae* ATCC 44774 and *Candida albicans* ATCC 10231.

The following examples are set forth to illustrate more clearly the principles and practice of this invention to one skilled in the art. As such, they are not intended to limit the invention, but are illustrative of certain preferred embodiments.

EXAMPLE I

Isolation of Antimicrobial Peptide from Catfish and Synthesis of its Derivatives First Step: Peptide Purification Catfish was injured by scratching the skin (16 cm$^2$) with a sandpaper and, 5 hours later, stunned by an electric shock. The proteinaceous epithelial mucosal layer was scraped off from the wounded site and an unwounded site, both. Each portion mucus (20 g) collected from the catfish skin was homogenized using a homogenizer, such as that sold by Waring, U.S.A., identified as "Waring blender" in 200 ml of an extraction solution (0.2 M sodium acetate, 0.2% Triton X-100 and 1 mM phenylmethylsulfonyl fluoride). Each of the homogenate was centrifuged at 20,000×g for 30 min in a centrifuge, such as that sold by Hitachi, Japan, under the brand name of Himac SCR20BR. Then, the supernatant was subjected to reverse-phase concentration using, for example, Sep-pak C18 cartridge (Millipore, U.S.A.) which had been activated with a solution of 80% acetonitrile in 0.1% (v/v) trifluoroacetic acid (TFA) (buffer A) and subsequently flushed with 0.1% (v/v) TFA (buffer B) to remove the excess acetonitrile. After being loaded with the supernatant, the Sep-Pak C18 cartridge was washed with 20 ml of buffer B, after which the peptides thus trapped in the cartridge were eluted with 6 ml of buffer A. The eluate was lyophilized and subsequently resuspended in buffer B. The resuspended sample was applied to a C18 reverse-phase high-performance liquid chromatography (HPLC) column (3.9× 300 mm, Delta Pak, Millipore), followed by the elution with a linear gradient of 0–80% acetonitrile in 0.1 TFA for 2 hours at a flow rate of 1 ml/min.

Figure 1B:
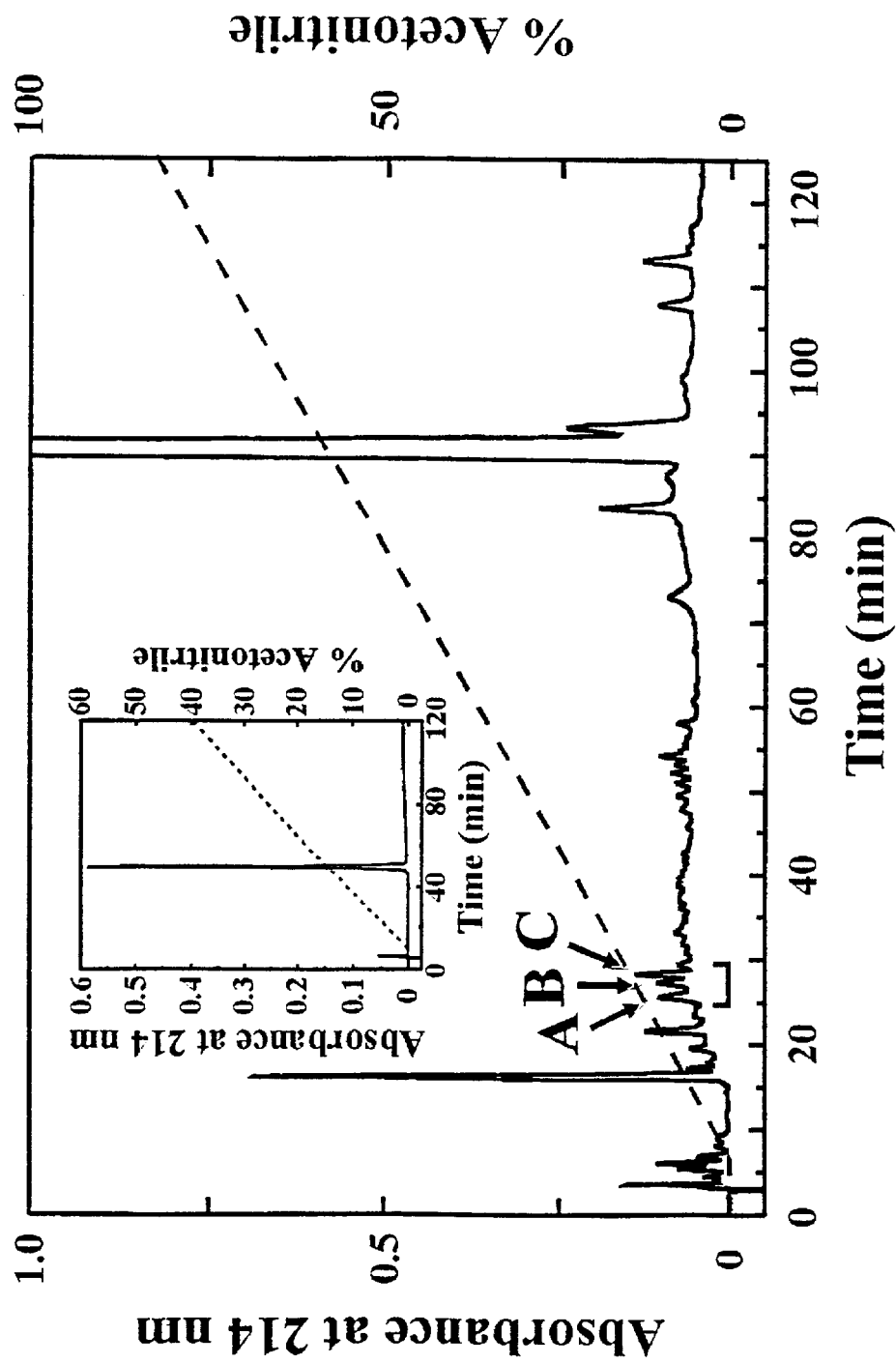

With reference to FIG. 1, reverse-phase HPLC analysis results of the eluates were shown. As apparent from the figure, the eluate from the wounded skin (FIG. 1b) had several peaks which were absent in the eluate from the unwounded skin (FIG. 1a). The peaks a, b and c in FIG. 1b were individually collected and assayed for antimicrobial activity. Of these three induced peaks, only peaks a and c showed antimicrobial activity. The antimicrobial activity assay revealed that peak a showed over 200 times stronger antimicrobial activity than peak c. Only peak a, which was of the strongest antimicrobial activity, was specifically purified by use of C18 reverse-phase HPLC and fully characterized. The purity of the antimicrobial peptide in peak a was confirmed to be over 95% homogeneous as determined by reverse-phase HPLC (FIG. 1b) and matrix associated laser desorption ionization mass spectroscopy (MALDI-MS).

The total amount of the purified antimicrobial peptide recovered in this step was about 0.1 μg per g of mucus and the purified antimicrobial peptide was named "parasin I" (derived from the genus name of the catfish 'Parasilurus').

Second Step: Molecular Mass and Amino Acid Sequencing of Parasin I

The molecular mass of parasin I was determined by MALDI-MS. Approximately 20 nmol of the lyophilized peptide was dissolved in a solution of 7% (w/v) sinapinic acid in 50% acetonitrile and mixed with a Pt probe. After removing the solvent in warm air, the peptide, absorbed to the Pt probe, was applied to a vacuum chamber and analyzed. Amino acid sequencing was performed by the automated Edman degradation method on a gas phase sequencer, such as that commercially available from Applied Biosystems, U.S.A., identified as "Model 477A". Amino acid homology searches were carried out by the computerized query of the GenBank™/EMBL Data Bank.

Figure 2:
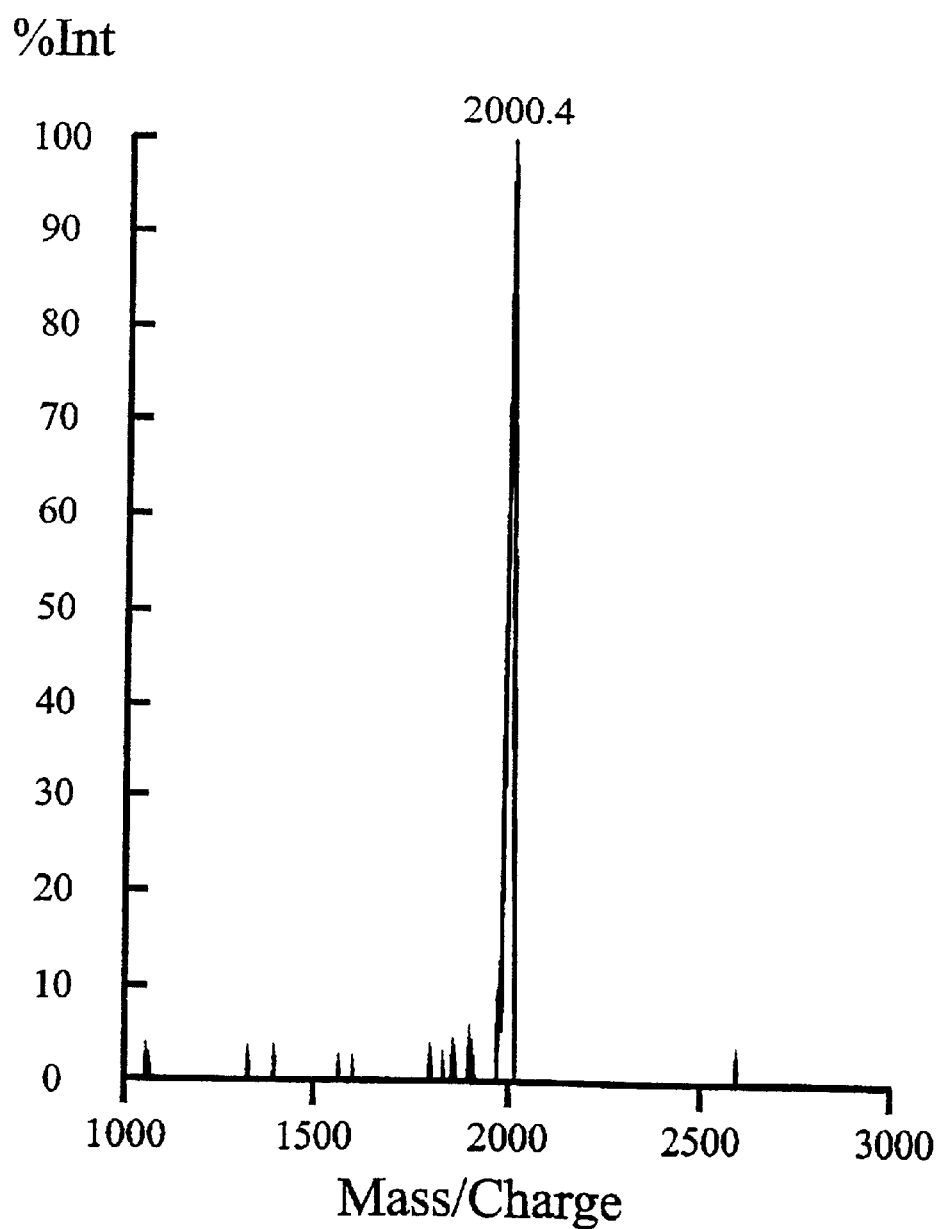
FIG. 2 is a mass/charge spectrum for the novel antimicrobial peptide, parasin I, isolated from catfish.

Referring to FIG. 2, there is a mass/charge spectrum for parasin I, taken by MALDI-MS. As seen, the molecular mass of parasin I was measured to be 2,000.4 Da. Amino acid sequence analysis revealed that parasin I was composed of 19 residues, including three arginines and five lysines, which contributed to the net charge of +8 (FIG. 3), and its complete amino acid sequence was Lys-Gly-Arg-Gly-Lys-Gln-Gly-Gly-Lys-Val-Arg-Ala-Lys-Ala-Lys-Thr-Arg-Ser-Ser(SEQ ID NO: 1). The molecular mass of parasin I obtained by MALDI-MS coincided well with that calculated from the amino acid sequence, indicating that posttranslational modification did not occur in parasin I. Amino acid sequence homology search demonstrated that parasin I was highly homologous to the N-terminal region of histone H2A, a replication-dependent protein. As seen in FIG. 3, parasin I was identical to the N-terminal of buforin I in eighteen of the nineteen residues, which corresponds to 95% homology. Parasin I also shared 89% homology with the N-terminal of human histone H2A.5.

Third Step: Synthesis of Parasin I Derivatives

Using an automatic peptide synthesizer, the peptides having the sequences shown in Table 1 were prepared. They were purified by C18 reverse phase HPLC (Waters Associates, U.S.A.).

TABLE 1

Amino Acid Sequences of Parasin Derivatives

| Peptides | Sequence |
|---|---|
| Seq. No. 2 | K G R G K Q G G K V R A K A K T R |
| Seq. No. 3 | K G R G K Q G G K V R A K A K |
| Seq. No. 4 | S S R T K A K A R V K G G Q K G R G K |

EXPERIMENT EXAMPLE I

Antibacterial and Hemolytic Activity Assays of Parasin I and its Derivatives

The parasin I and its derivatives obtained in Example I were lyophilized, resuspended in water and assayed for antimicrobial activity against B. subtilis ATCC 62037. The purity of the isolated peptides was analyzed by reverse-phase HPLC and MALDI-MS (Kratos Kompact MALDI, England). The antimicrobial activity of the samples was determined during each purification step by the radial diffusion assay using B. subtilis ATCC 62037 according to the method of Lehrer et al. ((1991) J. Immunol. Methods, 137, 167–173). A 20 ml culture of B. subtilis ATCC 62037 cell in mid-logarithmic phase was washed with 10 mM sodium phosphate buffer (NAPB), pH 7.4, at 40° C., and resuspended in 10 ml of the same buffer. A cell suspension containing 1×10$^6$ bacterial colony forming units (CFUs) was added to 6 ml of an underlayer agar (10 mM sodium phosphate, 1% (v/v) trypticase soy broth (TSB), 1% (w/v) agarose, pH 6.5) and this resulting mixture was poured into a Petri dish. Samples were added, at an amount of 5 μl, directly in 3-mm wells which were made on the solidified underlayer agar. After incubation for 3 hours at 37° C., the underlayer agar was covered with a nutrient-rich top agar overlay (6% (w/v) TSB, 1% (w/v) agarose) and incubated overnight at 37° C. Antimicrobial activity was determined by observing the zone of suppression of bacterial growth around the 3-mm wells. The minimal inhibitory concentrations (MICs) of the isolated peptide against the microorganisms were determined as described by Moore et al. ((1991) J. Biol. Chem., 266, 19851–19857). 100 μl microorganism suspensions (10$^5$ CFU/ml) in 3% (w/v) TSB were mixed with serial two-fold dilutions of the isolated peptide in a sterilized 96-well microtiter plate (Nunc, Denmark). The final concentration of the peptide ranged 0.5–200 μg/ml. The 96-well plate was incubated overnight at 37° C. and the inhibition of growth was determined by measuring the absorbance at 620 nm on a microplate reader, such as that sold by B10-Rad, U.S.A., under the brand name of Model 550. The MIC was defined as the lowest concentration of peptide that inhibited growth. In respect to the test for antimicrobial activity, 10 different microorganisms, including Gram-negative bacteria, Gram-positive bacteria and fungi were used. The results are given in Table 2, below. As apparent from Table 2, parasin I showed more potent antimicrobial activity than did other conventional peptides. What is noteworthy is that synthetic derivatives of parasin I had more potent antimicrobial activity than any other peptide. The MIC data of Table 2 exhibit that parasin I was approximately 12–100 times more potent than magainin 2, which was purified from Xenopus laevis, and up to 8 times than buforin I, which was isolated from Bufo bufo gagarizans.

TABLE 2

Minimal Inhibitory Concentrations Against Various Microbes

| | MIC (μg/ml) | | | | | |
|---|---|---|---|---|---|---|
| Microorganisms | Parasin I | Buforin I | Magainin 2 | Seq. No. 1 | Seq. No. 2 | Seq. No. 3 |
| Gram Positive | | | | | | |
| Bacillus subtilis | 1 | 4 | 50 | 0.5 | 0.5 | 1 |
| Staphylococcus aures | 2 | 4 | 50 | 1 | 1 | 2 |
| Streptococcus mutans | 1 | 8 | 100 | 0.5 | 0.5 | 1 |
| Pseudomonas putida | 2 | 4 | 50 | 2 | 2 | 2 |
| Gram Negative | | | | | | |
| Escherichia coli | 1 | 8 | 100 | 0.5 | 0.5 | 1 |
| Salinoneila typhimurium | 2 | 4 | 25 | 1 | 1 | 2 |
| Serratia sp. | 4 | 8 | 50 | 4 | 2 | 4 |
| Fungi | | | | | | |
| Cryptococcus neofotmans | 2 | 4 | 12 | 1 | 1 | 2 |
| Sacctharomyces cerevisiae | 2 | 4 | 25 | 1 | 2 | 2 |
| Candida aibicans | 2 | 4 | 25 | 1 | 1 | 4 |

The hemolytic activity of the antimicrobial peptide was assayed as described by Park et al. (9). Tests against human erythrocytes demonstrated that parasin I (200 μg/ml) caused only 0.2% hemolysis whereas melittin, a hemolytic peptide, effected 99.2% hemolysis at the same concentration.

EXPERIMENT EXAMPLE II

Determination of Secondary Structure of Parasin I

The secondary structure of parasin I was estimated using a spectropolarimeter in the absence or presence of trifluoroethanol (TFE). For circular dichroism (CD) analysis, peptide samples were dissolved in either 50 mM NAPB or 50% (v/v) TFE. The CD spectra were recorded at room temperature on a Jasco model J-715 spectropolarimeter (Jasco, Japan) with a cell path length of 1 mm. Scanning was executed five times per sample and these scan values were averaged over the wavelength range 200–250 nm. Ellipticity is reported as mean residue ellipticity [θ] (degrees cm$^2$ dmol$^{-1}$). The contents of α-helix, β-sheet and random coils were estimated as taught by Greenfield and Fasman ((1969) Biochemistry, 8, 4108–4116).

Figure 4:
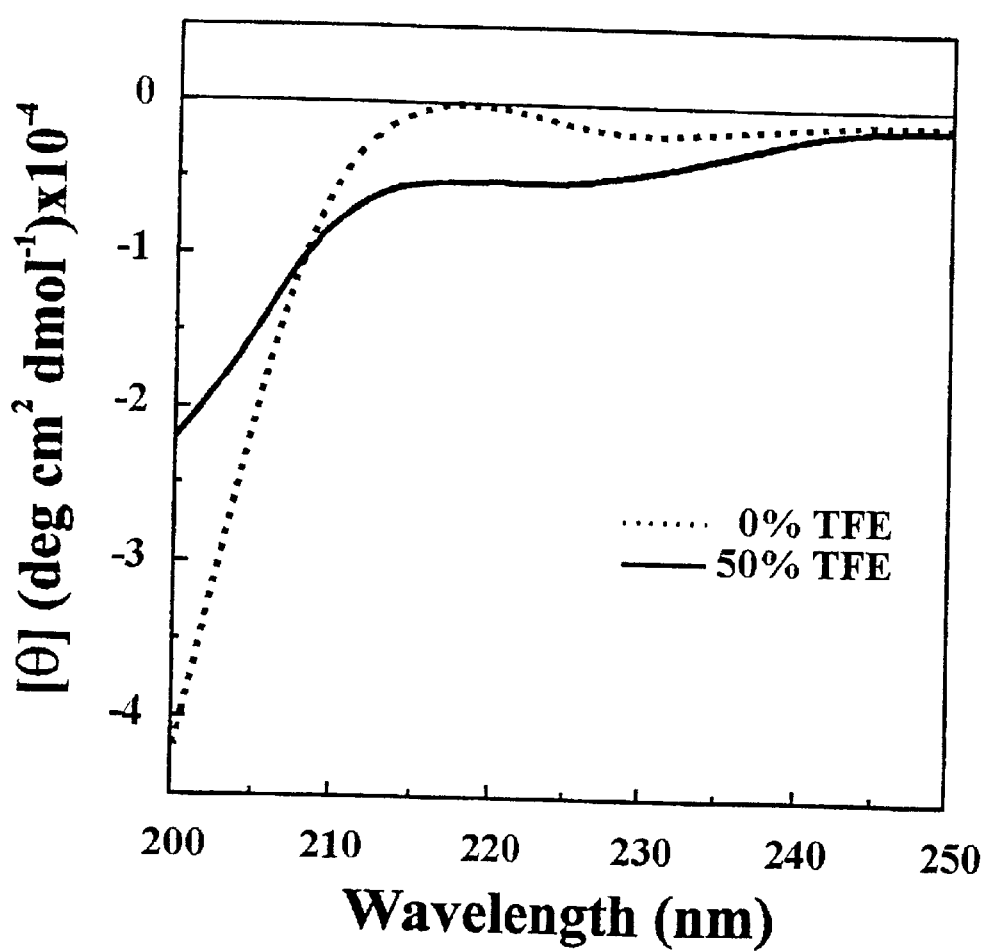
FIG. 4 shows the mean residue ellipticity of parasin I plotted against wavelength, which is measured by a spectropolarimeter in the absence or presence of trifluoroethanol.
Figure 5:
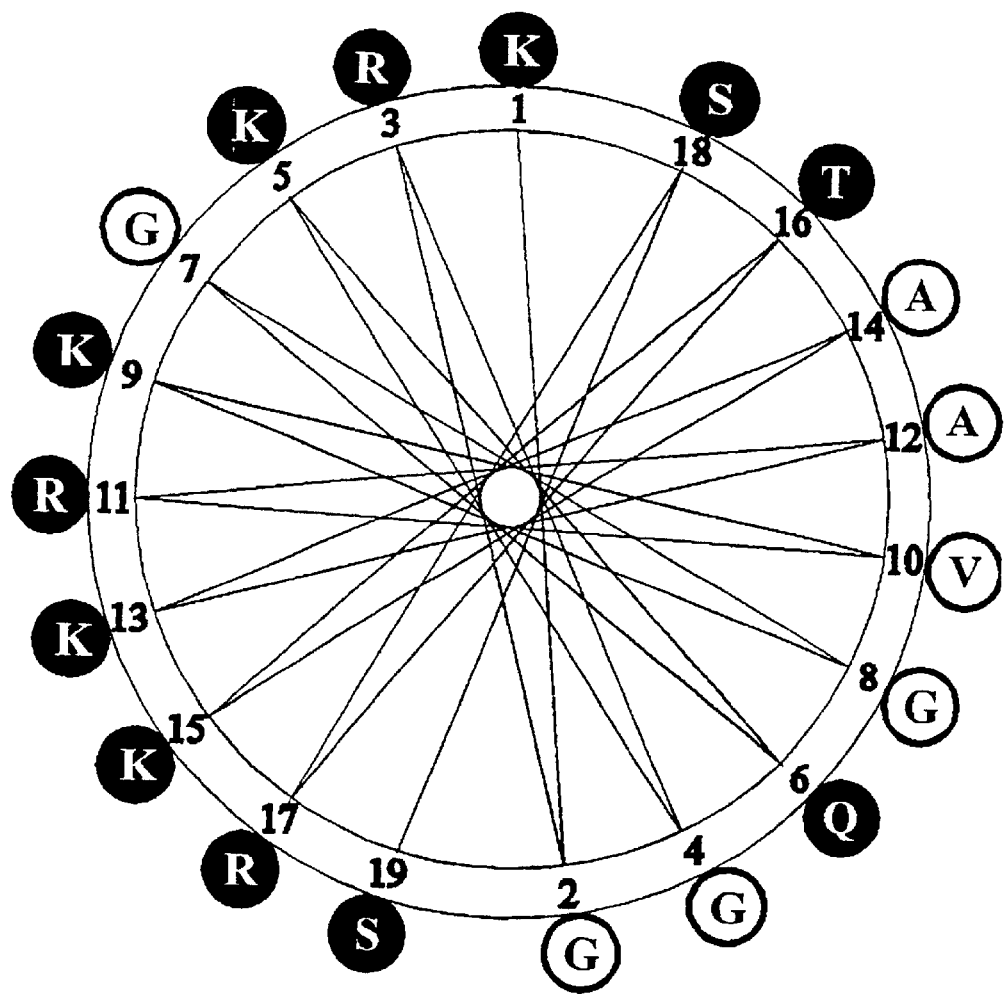
FIG. 5 is an axial projection diagram of parasin I drawn with 170° rotation per residue.

FIG. 4 shows these results. The CD spectra are baseline-corrected and smoothed by the algorithm provided by the manufacturer. When analyzed by the method of Greenfield and Fasman, the CD spectrum of parasin I in 50 mM NAPB indicated that the contents of α-helix, β-sheet and random coils were 11%, 33% and 56%, respectively. The addition of TFE, an α-helix inducing solvent, slightly increased the β-sheet content in parasin I. This result suggests that parasin I formed a β-strand, in both hydrophilic and hydrophobic environments, instead of the linear amphipathic α-helix which is common for many other antimicrobial peptides. An axial projection diagram of parasin I was drawn with 170° rotation per residue to determine whether it was possible for parasin I to form an amphipathic β-strand, as shown in FIG. 5. The axial projection formed a nearly perfect amphipathic β-strand with 7 of the 8 cationic residues on the hydrophilic side of the β-sheet plane.

INDUSTRIAL APPLICABILITY

As described hereinbefore, the antimicrobial peptide parasin I was isolated from catfish and its synthetic derivatives have potent antimicrobial activity against Gram-positive and Gram-negative bacteria and fungi and can prevent microbes from being developed on injured skin without any hemolytic activity. Therefore, the antimicrobial peptides of the present invention are useful as wound healing agents, trauma curing agents, mouthwash, eyewash, etc.

Although the invention has been described in detail by referring to certain preferred embodiments, it will be understood that various modifications can be made within the spirit and scope of the invention. The invention is not to be limited except as set forth in the following claims.

What is claimed is:

1. A peptide comprising the following sequence: KGRGKQGGKVRAKAKTRSS (SEQ ID NO: 1).

2. A peptide selected from the group consisting of
KGRGKQGGKVRAKAKTRSS (SEQ ID NO: 1)
KGRGKQGGKVRAKAKTR (SEQ ID NO: 2)
KGRGKQGGKVRAKAK (SEQ ID NO: 3); and
SSRTKAKARVKGGQKGRGK (SEQ ID NO: 4).

3. An antibacterial peptide comprising the following sequence:
KGRGKQGGKVRAKAKTRSS (SEQ ID NO: 1).

4. An antibacterial peptide selected from the group consisting of
KGRGKQGGKVRAKAKTRSS (SEQ ID NO: 1)
KGRGKQGGKVRAKAKTR (SEQ ID NO: 2)
KGRGKQGGKVRAKAK (SEQ ID NO: 3); and
SSRTKAKARVKGGQKGRGK (SEQ ID NO: 4).

5. A composition containing a suitable carrier, and a peptide in an amount effective to inhibit bacterial growth, wherein said peptide is selected from the group consisting of:
KGRGKQGGKVRAKAKTRSS (SEQ ID NO: 1)
KGRGKQGGKVRAKAKTR (SEQ ID NO: 2);
KGRGKQGGKVRAKAK (SEQ ID NO: 3); and
SSRTKAKARVKGGQKGRGK (SEQ ID NO: 4).

6. A composition comprising a suitable carrier, and a peptide selected from the group consisting of:
KGRGKQGGKVRAKAKTRSS (SEQ ID NO: 1)
KGRGKQGGKVRAKAKTR (SEQ ID NO: 2);
KGRGKQGGKVRAKAK (SEQ ID NO: 3); and
SSRTKAKARVKGGQKGRGK (SEQ ID NO: 4).

7. A method of inhibiting bacterial growth comprising contacting a target area with a peptide according to claim 2, wherein said peptide is administered in an amount effective to inhibit bacterial growth, and for a time and under conditions effective to inhibit bacterial growth.

8. A method of inhibiting fungal growth comprising contacting a target area with a peptide according to claim 2, wherein said peptide is administered in an amount effective to inhibit fungal growth, and for a time and under conditions effective to inhibit fungal growth.

* * * * *